United States Patent
Turdiu et al.

[19]

[11] Patent Number: 6,164,966
[45] Date of Patent: Dec. 26, 2000

[54] REMOVAL OF DENTAL CARIES WITH HIGH SPEED WATER JET

[75] Inventors: Parid Turdiu, West New York; Eugene Irving Gordon, Mountainside; Joel Hasen, New Providence, all of N.J.; Ronald B. Odrich, Bronx, N.Y.; Alan A. Winter, Morristown, N.J.

[73] Assignee: Medjet, Inc., Edison, N.J.

[21] Appl. No.: 09/271,403

[22] Filed: Mar. 17, 1999

[51] Int. Cl.$^7$ .................................................. A61G 17/02
[52] U.S. Cl. ............................................. 433/80; 433/216
[58] Field of Search .......................... 433/80, 89, 216; 601/162, 161, 165

[56] References Cited

U.S. PATENT DOCUMENTS

| 3,863,628 | 2/1975 | Vit | 433/89 |
| 4,012,842 | 3/1977 | Vit | 433/89 |

*Primary Examiner*—Nicholas D. Lucchesi
*Attorney, Agent, or Firm*—Greenberg Traurig

[57] ABSTRACT

A method and device for the high speed fluid (preferably water) jet removal of dental caries. The water jet is of a controlled upper and lower speed and pressure with a low speed and pressure being of at least 5 to 10 kpsi, sufficient to pierce and flush decayed tissue of a caries with a small beam fluid jet diameter. A pulsed or continuous fluid jet is used to remove and completely flush caries material from a tooth in a time period of under a second with a maximum stagnation pressure of about 30 kpsi, at which point healthy dentin is affected. A coherent or pseudo-coherent water jet operating at high stagnation pressure (range 10,000 to 20,000-psi and no more than 30-kpsi), in a brief burst ($\approx$1 second) and small beam diameter (30 to 100-$\mu$m) will cleanly remove caries without damage to the tooth structure in particular the sound dentin at the boundary of the caries. No anaesthetic is accordingly required in the absence of a possible exposed nerve.

18 Claims, 2 Drawing Sheets

REMOVAL OF DENTAL CARIES WITH HIGH SPEED WATER JET

FIELD OF THE INVENTION

This invention relates to methods and devices for the removal of the dental caries and in particular those methods and devices with lessened damage to healthy dentin and reduced pain for the patient.

BACKGROUND OF THE INVENTION

At present the method of choice for removing decayed dentin and other structure in a dental caries associated with a cavity, preparatory to filling the tooth, is a mechanical dental drill. The dental drill is guided by a dentist to drill into a tooth until all remnants of the caries are separated from the healthy dentin. Thereafter a low pressure water jet or air spray is used to wash or remove the caries material from the tooth. The process involved entails a certain degree of inevitable pain as a result of small portions of healthy dentin being removed as well. In addition, the high pitched whine of a dental drill is often accompanied by psychological trauma of the patient. In fact, fear of the dental drill is a major reason that people in need of dental care postpone visits to a dentist.

Recently research has involved the use of lasers to selectively burn out the caries prior to filling of the tooth. Though the lasers are silent they nevertheless also inevitably remove a small portion of healthy dentin.

With prior art methods of caries removal, the process is slow and requires pauses for inspection of the cavity (to ascertain the stage of removal) since during drilling, the caries is not visible.

SUMMARY OF THE INVENTION

It is an object of the present invention to provide a method and device which utilizes fluid and specifically water lets, normally used in a low pressure mode, to rinse debris from drilled teeth cavities and trapped between teeth, to effect the actual removal and rinsing away of caries material from teeth.

It is a further object of the present invention to provide such water jet with a pressure sufficient to effect separation of caries material (decayed dentin) from healthy dentin but without affecting the healthy dentin, whereby only caries material is efficiently removed with reduced pain and little or no effect on underlying healthy dentin.

It is yet a further object of the present invention to provide the controlled high pressure water jet with a beam diameter sufficiently small enough to simultaneously effect the separation of the caries material from the tooth and the flushing away thereof to leave a tooth in cleaned condition for immediate filling.

It is still yet another object of the present invention to provide a means for complete removal of caries material from a cavity of a tooth without the necessity of periodic inspection and wherein the entire procedure is silent and takes less than a is second.

It is still yet another object of the present invention to provide a means for complete removal of caries material from a cavity of a tooth without the necessity of u sing anesthesia.

Generally the present invention comprises a method and device for the high speed fluid (preferably water) jet removal of dental caries. The present invention utilizes a unique characteristic of water jets, not present in mechanical drills and lasers, of adjustable pressure and temporal control to provide the selective, automatic and complete removal of decayed dentin from healthy dentin, without any residual effect on the healthy dentin.

It is a recognized characteristic of dental caries that the decay of dentin causes the softening thereof as compared to healthy dentin.

The method for the removal of dental caries in accordance with the present invention comprises the steps of:

a) placing a source for a fluid jet such as a water jet adjacent to and directed at the exposed surface of a dental H caries; and b) penetrating the dental caries with the fluid. jet from said source for a time and with a force sufficient to permit the fluid jet to hit a surface of healthy dentin and be deflected thereby, wherein the fluid jet has a stagnation pressure sufficient to penetrate the dental caries but not sufficient to penetrate the dentin, whereby the dental caries is removed from the surface of the dentin and flushed out of the tooth.

According to the present invention, a water or fluid jet is adjusted to penetrate the soft caries material but to be deflected by the harder healthy dentin. In accordance with the present invention a fluid or water jet of small cross sectional diameter (maximum diameter being equal to the diameter of the caries and preferably much smaller) is provided with a controlled lower stagnation pressure of at least 5 and preferably at least 10 kpsi (this is on the order of at least 50 times the pressure of a Water pik® device used for pressurized cleaning between teeth). This pressure is sufficient to penetrate the dental caries material but will not affect the harder healthy dentin. The controlled maximum stagnation pressure is about 30 kpsi for a 1 second duration (25 kpsi if the water jet is sustained for a few seconds), at which point healthy dentin begins to be affected.

With a water jet of a pressure within the above range, directed into the caries material (to maximize effectiveness and to minimize inadvertent engagement with soft tissue in the mouth of a patient) the water penetrates the relatively soft caries material and is stopped at the caries-dentin interface. The water of the water jet is then deflected along the caries-dentin interface thereby effecting a full separation between the caries material and the healthy dentin without damage or effect on the healthy dentin. At the same time the water serves to flush the severed material from the cavity, thereby simultaneously completely cleaning out the cavity for subsequent filling. The deflection further serves to substantially lessen the water pressure of the water which exits the cavity whereby engagement with adjacent soft tissue is at most a vigorous rinsing.

For small depth and diameter cavities it is preferred to utilize water pressure at the low end of the pressure range and for larger cavities at the higher end of the range to enhance effectiveness while reducing residual water pressure which exits the cavity.

The water jet may either be pulsed or continuous with the former providing a slightly better rinsing flush. With either type of water jet, total removal time is on the order of 1 second or less and since healthy dentin is not affected, no inspection steps are necessary. The procedure is silent, i.e., not accompanied by any traumatizing sound.

A coherent or pseudo-coherent water jet operating at high stagnation pressure (range 10,000 to 20,000 psi and no more than 30 kpsi), in a brief burst (≈1 second) and small beam diameter (30 to 100 μm) will cleanly remove caries without damage to the tooth structure in particular the sound dentin at the boundary of the caries. Since no healthy dentin is affected no anaesthetic is required unless x-rays indicate the presence of an exposed nerve (as with use of a drill, an anaesthetic is required) Though in such case pain is inevitable, it is of much shorter duration as compared to prior art caries removal methods.

A device for removing dental carries in accordance with the present invention comprises a source for a pressurized fluid jet, a dispensing nozzle, actuating means for actuating the pressurized fluid jet, and means for controlling pressure of said pressurized fluid jet to a stagnation pressure sufficient to penetrate the dental caries but not sufficient to penetrate the dentin, whereby the dental caries is removed from the surface of the dentin and flushed out of the tooth.

The above and other objects, features and advantages of the present invention will become more evident from the following discussion and drawings in which:

SHORT DESCRIPTION OF THE DRAWINGS

FIG. 1 is a schematic cross sectional view of a tooth with a dental caries;

FIGS. 2a–c are schematic cross sectional sequential views of the tooth of FIG. 1 having caries material removed therefrom by a water jet of the present invention; and FIG. 3 is a more detailed schematic cross sectional view of the tooth of FIG. 1 showing the various zones of a tooth having a caries therein and the varying effects of the water jet of FIGS. 2a and 2b thereon.

DETAILED DESCRIPTION OF THE INVENTION

Figure 1:
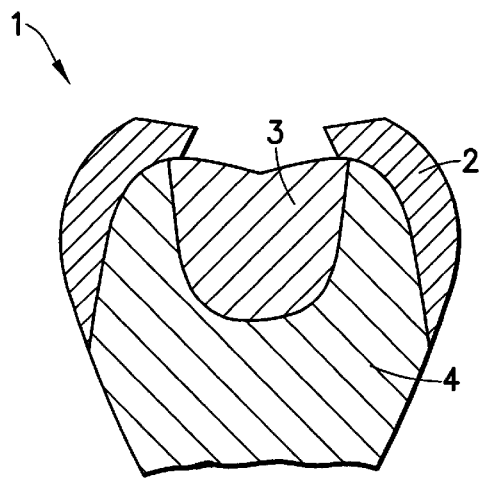

With the use of a controlled pressure water jet, in accordance with the present invention, there is a complete removal of decayed and infected tissue within the caries with no damage to healthy dentin and the process is fast and quiet. Room temperature, distilled plus tap water may be utilized for the water jet though sterilized water is preferred (the water penetrates tubules within the dentin and sterilized water is therefore preferred though not required). Since the process is essentially a high-powered flush, there is no odor, such as the burning characteristic with use drills and lasers and no threatening sounds which accompany use of drills or burrs.

Very little water is required and the devices for providing the requisite pressure and control are relatively small and inexpensive and can be cleaned by washing in sterilizing fluid rather than by autoclaving. The actual nozzles of the water jet placed in the patient's mouth should be angularly adjustable to reach caries in varying tooth locations and may be disposable between patients without excessive cost.

Use of a water jet device in accordance with the present invention is simple and highly controlled and entails selecting an appropriate pressure within the working range (depending on the type and dimension of the caries being cleaned), placing the water jet nozzle directly adjacent an exposed surface of the caries and activating the water jet for about one second. The caries is cleanly removed with no damage to any underlying dentin and accordingly little or no pain . The tooth is then in pristine cleaned condition for filling. If a nerve is exposed beneath the caries, use of an anaesthetic is also required as with normal prior art drilling procedures.

A factor in determining the piercing or 'damaging' power of the water jet is orifice diameter which determines the force being applied to the caries. Accordingly, the effective upper limit for the nozzle diameter is about 200 to 300 $\mu$m and the lower limit is about 10 to 20 $\mu$m. In addition, it is noted that a very large diameter water jet may interfere with an efficient water backwash.

It is believed that a continuous flow water jet generates a superior backwash, whereas a pulsed flow water jet may be less painful, especially with exposed nerves. Pulsed jets are generally more effective in cleaning because spent water does not get in the way when the next pulse starts. Both types are within the purview of the present invention A practical water jet control device for a dentist includes a trigger, such as a foot pedal, which delivers about 1 sec of flow to the nozzle handpiece to minimize the hazards of damaging of soft tissue in the patient's mouth.

In order to minimize damage to other soft tissue in the patient's mouth, it is preferred to use an aiming mechanism, which runs the water jet at a harmless pressure to spot the targeted caries. Other devices include a metal guide or a light guide to allow treatment at a difficult angle or geometry.

DETAILED DESCRIPTION OF THE DRAWINGS AND THE PREFERRED EMBODIMENT

With reference to the drawings, in FIG. 1 a typical molar tooth 1 is shown with an outer enamel or hard tissue layer 2, a soft tissue caries segment 3 and a hard tissue dentin 4 which comprises the tooth structure. The caries segment 3 is comprised of soft decayed dentin and must be removed to prevent further decay of dentin. The volume from which the caries is removed is then filled with a dental filler material to restore tooth function and prevent further decay.

Figure 2A:
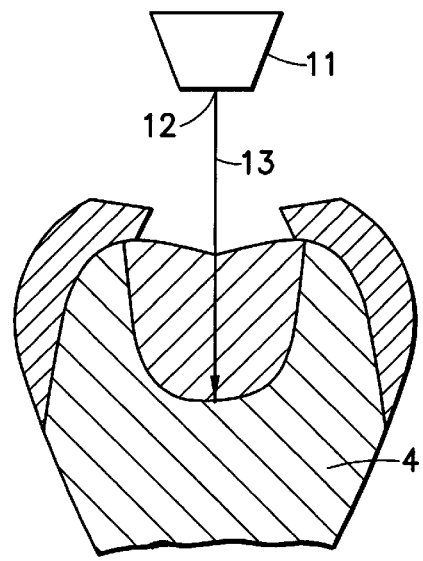
Figure 2B:
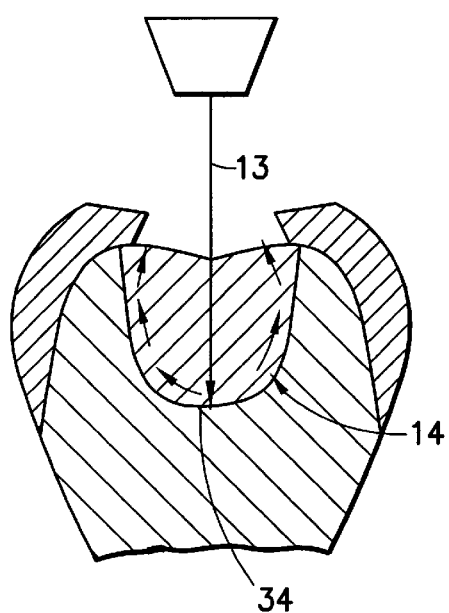
Figure 2C:
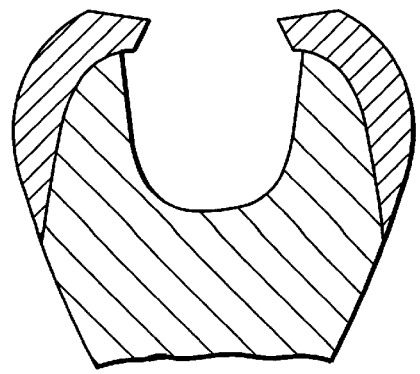

As shown in FIGS. 2a–c, the caries 3 is removed in accordance with the present invention by initial placement of a high pressure water jet source 10 with nozzle 11, such that water jet orifice 12 is slightly above the exposed surface of caries 3. For efficient operation the orifice is aimed at the approximate center of the caries surface, as shown in FIG. 2a. The water jet 13 penetrates the caries material 3 until it hits the caries-dentin interface 34. As shown in FIG. 2b, the water jet 13 bounces off the hard healthy dentin 4 to form a backwash 14 (designated by the arrows) which separates and flushes the caries material 3 from the healthy dentin 4 at the interface 34 without affecting the dentin. As shown in FIG. 2c, a pristine empty cavity remains for immediate filling.

The nozzle 11 is constructed of a maneuverable material such as discardable stainless steel tubing which can be bent by a bending tool to assume a position relative to a specific caries as required. Alternatively, interchangeable nozzles of different configurations may be used for appropriate situations.

Figure 3:
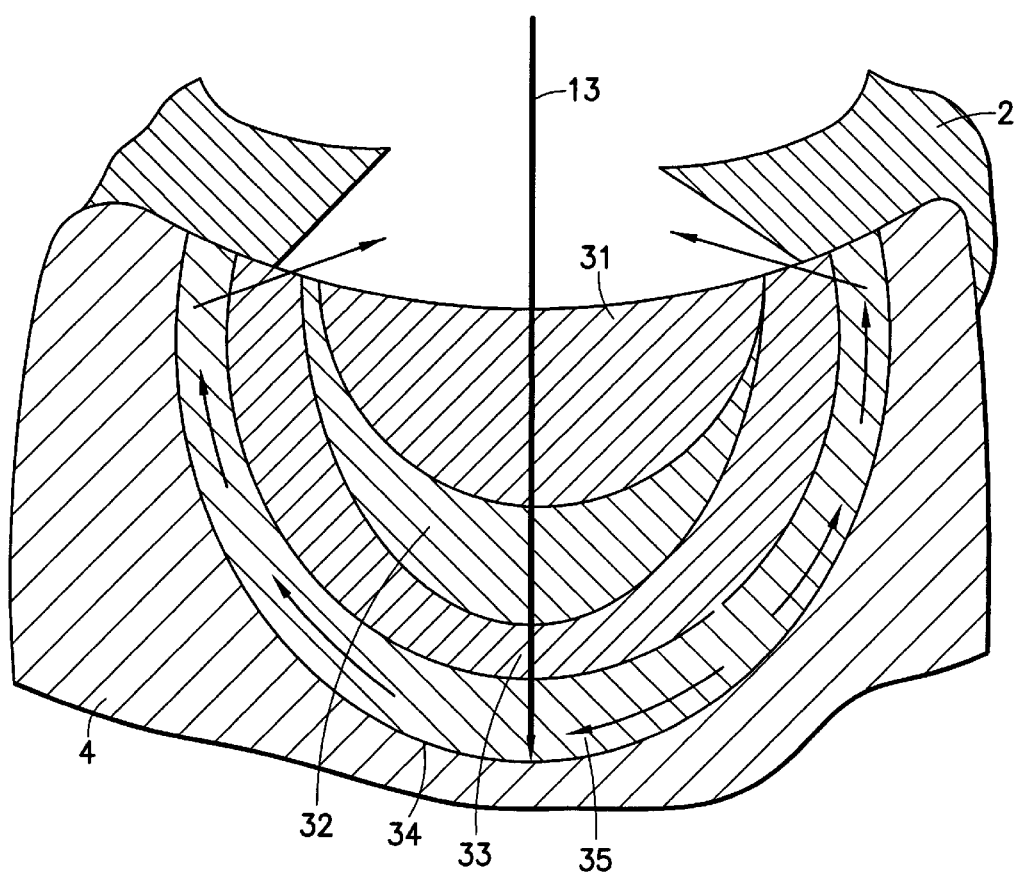

As shown in greater detail in FIG. 3, the water jet 13 is directed at the low bacterial zone of dentin caverns 31, between portion of the hard enamel 2. The water jet penetrates zone caverns 31, zone of initial infection 32, demineralization zone 33 and transparent dentin 35 until it hits the harder intact dentin 4 at caries-dentin surface 34. The water jet is pressure controlled, as described, to effect the penetration of the softer tissue and deflection off the harder dentin with the backwash as shown by the arrows with a pristine empty cavity being left behind ready to be filled by the dentist.

It is understood that the above description and drawings are illustrative of the present invention and that changes in method steps, components and materials and the like are possible without departing from the scope of the present invention as defined in the following claims.

What is claimed is:

1. A method for the removal of dental caries comprising the steps of:
   placing a source for a water jet adjacent and directed at an exposed surface of a dental carries comprised of caries material; and
   penetrating the dental caries with a water jet from said source for a time and with a force sufficient to permit the water jet to hit a surface of healthy dentin at a interface between the caries material and the healthy dentin and be deflected thereby, thus foaming a backwash which mechanically separates and flushes the caries material away from the healthy dentin without substantilly affecting the dentin,
   wherein the water jet consists essentially of pressurized water and has a stagnation pressure sufficient to penetrate the dental caries but not sufficient to penetrate the dentin.

2. The method of claim 1, wherein the water jet is one of continuous and pulsed.

3. The method of claim 1, wherein the stagnation pressure ranges between 5-kpsi and 30-kpsi.

4. The method of claim 3, wherein the pressure ranges between 10-kpsi and 20-kpsi.

5. The method of claim 4, wherein the water jet has a cross sectional diameter within the range of 10 to 300-$\mu$m.

6. The method of claim 5, wherein the water jet has a cross sectional diameter within the range of 20 to 200-$\mu$m.

7. The method claim 6, wherein said time is less than one second.

8. A device for mechanically removing dental caries from a tooth in accordance with the method of claim 1, comprising a source for a pressurized water jet, said jet consisting essentially of pressurized water, a dispensing nozzle, actuating mans for actuating the pressurized water jet, and means for controlling pressure of said pressurized water jet to a stagnation pressure sufficient to penetrate the dental caries but not sufficient to penetrate the dentin, whereby saids jet produces a backwash at an interface between said caries and healthy dentin which mechanically separates and flushes caries material away from the healthy dentin and out of the tooth without substantially affecting the dentin.

9. The device of claim 8 wherein the device comprises means for actuating the water jet as a continuous jet.

10. The device of claim 8 wherein the device comprises means for actuating water as a pulsed jet.

11. The device of claim 8, wherein the means for controlling stagnation pressure controls the stagnation pressure in a range between 5-kpsi and 30-kpsi.

12. The device of claim 11, wherein the pressure ranges between 10-kpsi and 20-kpsi.

13. The device of claim 8, wherein the nozzle has a water jet dispensing orifice with a cross sectional diameter within the range of 10 to 300-$\mu$m.

14. The device of claim 13, wherein the orifice has a cross sectional diameter within the range of 20 to 200-$\mu$m.

15. The device of claim 8, wherein the device comprises means for actuating the water jet for no more than one second.

16. The device of claim 8, wherein the nozzle is interchangeable relative to the device for use with placement selected nozzles adapted to be juxtaposed with differently positioned caries in teeth.

17. The device of claim 8, wherein the nozzle comprises means for adopting its angular relation to caries of different teeth and locations.

18. The device of claim 8, wherein the device comprises aiming guide means adapted to guide the water jet directly to the caries.

* * * * *

UNITED STATES PATENT AND TRADEMARK OFFICE
CERTIFICATE OF CORRECTION

PATENT NO. : 6,164,966
DATED : December 26, 2000
INVENTOR(S) : Parid Turdiu et al.

It is certified that error appears in the above-identified patent and that said Letters Patent is hereby corrected as shown below:

Column 5, claim 1,
Line 3, change "stops" to -- steps --;
Line 5, change "carries" to -- caries --;
Line 9, change "a" to -- an --;
Line 11, change "foaming" to -- forming --;
Line 14, change "substantilly" to -- substantially --.

Column 5, claim 8,
Line 35, change "mans" to -- means --;

Column 6, claim 8,
Line 38, change "saids" to -- said --.

Signed and Sealed this

Sixteenth Day of April, 2002

Attest:

JAMES E. ROGAN
Director of the United States Patent and Trademark Office

Attesting Officer